United States Patent [19]

Murtiashaw

[11] Patent Number: 5,248,820
[45] Date of Patent: Sep. 28, 1993

[54] CRYSTALLINE N-(S-3-METHYLHEPTANOYL)-D-GAMMA-GLUTAMYL-GLYCYL-D-ALANINE, AND PROCESSES AND INTERMEDIATES THEREFOR

[75] Inventor: Charles W. Murtiashaw, North Stonington, Conn.

[73] Assignee: Pfizer Inc., New York, N.Y.

[21] Appl. No.: 968,558

[22] Filed: Oct. 29, 1992

Related U.S. Application Data

[62] Division of Ser. No. 852,858, Mar. 17, 1992, Pat. No. 5,185,464, which is a division of Ser. No. 341,350, Feb. 21, 1989, Pat. No. 5,136,020.

[51] Int. Cl.$^5$ .............................................. C07C 51/16
[52] U.S. Cl. ...................................... 562/538; 562/545
[58] Field of Search ................................ 562/538, 545

[56] References Cited

U.S. PATENT DOCUMENTS

| | | | |
|---|---|---|---|
| 3,985,722 | 10/1976 | Yoshida et al. | 260/112 R |
| 4,401,658 | 8/1983 | Bouchaudon et al. | 424/177 |
| 4,564,620 | 1/1986 | Ohno et al. | 514/337 |
| 4,565,653 | 1/1986 | Ives et al. | 260/112.5 R |
| 4,767,743 | 8/1988 | Rizzi | 514/18 |

FOREIGN PATENT DOCUMENTS

| | | |
|---|---|---|
| 976975 | 12/1964 | United Kingdom . |
| 1167776 | 10/1969 | United Kingdom . |

OTHER PUBLICATIONS

Oppolzer et al., Helvetica Chimica Acta, vol. 68, pp. 212–215 (1985).
Mukaiyama et al., Chemistry Letters, pp. 913–916 (1981).
Soai et al., J. Chem. Soc., Chem. Commun., pp. 469–470 (1985).
Posner et al., J. Am. Chem. Soc., vol. 103, No. 10, pp. 2886–2888 (1981).
Meyers et al., J. Am. Chem. Soc., vol. 98, No. 8, pp. 2290–2294 (1976).
Chemical Abstracts, v. 47, abstract No. 9268d (1953); abstracting Gol'mov, Zhur. Obshchei Khim., v. 22, 1944–53 (1952).
Eschinazi, J. Org. Chem., v. 26, 3072–3076 (1961).
House, "Modern Synthetic Reactions", 2nd ed., Benjamin, Inc., (1972) pp. 263, 269, 274–275.
LeBel et al., J. Org. Chem., v. 36, pp. 2440–2448 (1971).
Herberman et al., *13th International Congress of Chemists*, 1983, pp. 203/19–203/35.

*Primary Examiner*—José G. Dees
*Assistant Examiner*—Porfirio Nazario
*Attorney, Agent, or Firm*—Peter C. Richardson; Gregg C. Benson; Mervin E. Brokke

[57] ABSTRACT

A process and intermediates for the manufacture of S-3-methylheptanoic acid from S-citronellol; a novel crystalline form of immunoregulatory N-(S-3-methylheptanoyl)-D-gamma-glutamyl-glycyl-D-alanine, an immunoregulatory agent; and an improved process and intermediates therefor.

8 Claims, No Drawings

CRYSTALLINE N-(S-3-METHYLHEPTANOYL)-D-GAMMA-GLUTAMYL-GLYCYL-D-ALANINE, AND PROCESSES AND INTERMEDIATES THEREFOR

This is a division of application Ser. No. 852,858 filed Mar. 17, 1992, now U.S. Pat. No. 5,785,464 which is a division of Ser. No. 07/341,350, filed on Feb. 21, 1989, now U.S. Pat. No. 5,136,020 as a request for U.S. examination of International application No. PCT/US86/01775, filed on Aug. 27, 1986, now U.S. Pat. No. 5,136,020.

The present invention is directed to an advantageous process for an immunoregulatory agent of the formula

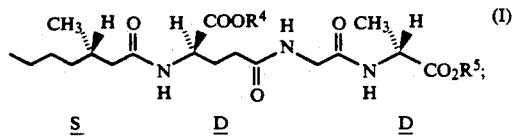

wherein $R^4$ and $R^5$ are each hydrogen or one of $R^4$ and $R^5$ is hydrogen and the other is $(C_1-C_6)$ alkyl or $(C_6-C_8)$cycloalkylmethyl; to a particular advantageous crystalline form of that agent when $R^4$ and $R^5$ are hydrogen; to a process and intermediates for the manufacture of S-3-methyl-6-heptenoic acid (VId, below) and S-3-methylheptanoic acid, the latter of the absolute stereochemical formula

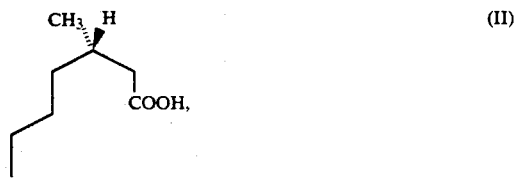

having utility as intermediates in the synthesis of the compound of the formula (I); to an improved process for the manufacture of the compound of the formula (I); and to immunoregulatory agents (or precursors) of the absolute stereochemical formula

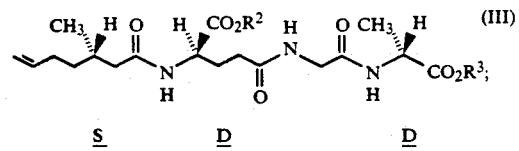

where $R^2$ and $R^3$ are each hydrogen (IIIa) or $R^2$ and $R^3$ are each independently $(C_1-C_6)$alkyl, $(C_6-C_8)$cycloalkylmethyl or benzyl (IIIb).

The above heptanoic and heptenoic acids are prepared from readily available S-citronellol (also known as S-(−)-beta-citronellol, beta-rhodinol and S-(−)-3,7-dimethyl-6-octen-1-ol), a compound which is employed in perfumery.

Optically pure S-3-methylheptanoic acid (II) was originally prepared from the corresponding racemate in unspecified yield by multiple crystallizations of the quinine salt at −15° C. [Levene et al., J. Biol. Chem., 95, pp. 1-24, 1932, at page 18, there called 2-n-butyl-butyric acid-4]. Optically active 3-methylheptanoic acid has subsequently been produced by a number of other methods (Soai et al., J. Chem. Soc., Chem. Commun. 1985, pp. 469-470; Oppolzer et al., Helv. Chim. Acta. 68, pp. 212-215 (1985); Ohno et al., U.S. Pat. No. 4,564,620 (1986); Mori et al., Synthesis 1982, pp. 752-753; Oppolzer et al., Helv. Chim. Acta. 64, pp. 2808-2811 (1981); Mukaiyama et al., Chem. Lett. 1981, pp. 913-916; Posner et al., J. Am. Chem. Soc. 103, pp. 2886-2888 (1981); Mukaiyama et al., Bull. Chem. Soc. Japan, 51, pp. 3368-3372 (1978); Meyers et al., J. Am. Chem. Soc. 98, pp. 2290-2294 (1976)] but these preparations generally suffer from one or more disadvantages (the maximum possible yield is 50%, with disposal of at least 50% of the undesired byproduct required; the product acid is not optically pure; use of organometallic reagents, difficult to handle on a large scale, is required; overall yields are low; and/or the required reagents are not readily available).

The relatively new field of immunopharmacology, and particularly that segment thereof which deals with immunomodulation, continues to develop at a rapid pace. A variety of naturally occurring compounds has been investigated, including the tetrapeptide tuftsin, known chemically as N²-[1-(N²-L-threonyl-L-lysyl)-L-prolyl]-L-arginine. Much attention has been directed to synthetic peptidoglycan derivatives, especially those known as muramyl dipeptides.

The immunoregulatory agent of the formula (I), generally as an amorphous lyophilate when $R^4=R^5=$hydrogen, and their method of use were earlier disclosed in copending PCT Application Ser. No. PCT/US85/02351, filed Nov. 25, 1985. Since that application is not yet publically available, preparation of these compounds and their method of use have been incorporated into the present disclosure in support of utility.

Other immunostimulant peptides have been described in a number of patent specifications:

L-Alanyl-alpha-glutaric acid N-acyl dipeptides in German 3,024,355, published Jan. 15, 1981;

tetra- and penta-peptides containing D-alanyl-L-glutamyl moieties or L-alanyl-D-glutamyl moieties in British 2,053,231, published Feb. 4, 1981 and German 3,024,281, published Jan. 8, 1981, respectively;

N-acyl-alanyl-gamma-D-glutamyl tripeptide derivatives in which the C-terminal amino acid is lysine or diaminopimelic acid in German 3,024,369, published Jan. 15, 1981;

lactoyl tetrapeptides composed of N-lactylalanyl, glutamyl, diaminopimelyl and carboxymethylamino components in EP-11283, published May 23, 1980;

polypeptides having the formula (A)

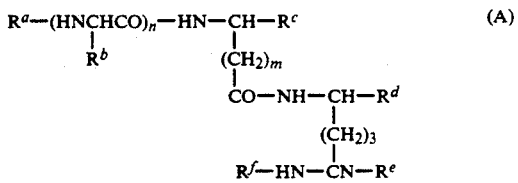

wherein $R^a$ is hydrogen or acyl; $R^b$ is inter alia hydrogen, lower alkyl, hydroxymethyl, benzyl; $R^c$ and $R^d$ are each hydrogen, carboxy, —$CONR^gR^h$ wherein $R^g$ is hydrogen, lower alkyl optionally substituted with hydroxy; and $R^h$ is mono- dicarboxy lower alkyl; $R^e$ is hydrogen or carboxy with the proviso that when one of $R^d$ and $R^e$ is hydrogen, the other is carboxy or —$CONR^gR^h$; $R^f$ is hydrogen; m is 1 to 3 and n is 0 to 2, and derivatives thereof in which the carboxy and amino groups are protected are disclosed in U.S. Pat. Nos. 4,311,640 and 4,322,341; EP applications 25,482; 50,856; 51,812; 53,388; 55,846 and 57,419; and peptides similar to those of the above formula (A), but wherein R[4] forms a basic aminoacid moiety (Ives et al., U.S. Pat. No. 4,565,653; EP application 157,572) or a heterocyclic aminoacid (Ives, EP application 178,845).

Kitaura et al., J. Med. Chem., 25, 335-337 (1982) report N[2](gamma-D-glutamyl)-meso-2(L),2(D)-diaminopimelic acid as the minimal structure capable of eliciting a biological response characteristic of compound of the formula (A) wherein n is 1; $R^a$ is $CH_3CH(OH)$—CO—; $R^b$ is $CH_3$; each of $R^c$ and $R^e$ is —COOH; $R^4$ is —CONHCH$_2$COOH; and $R^f$ is H. Said compound of formula (A) is known as FK-156.

SUMMARY OF THE INVENTION

We have now found a more stable, crystalline form of the immunoregulatory compound, N-(S-3-methylheptanoyl)-D-gamma-glutamyl-glycyl-D-alanine, of the formula (I) above wherein $R^4=R^5=$hydrogen.

We have also found efficient processes for the manufacture of intermediates S-3-methyl-6-heptenoic acid (VId, below) and S-3-methylheptanoic acid (II, above) of high optical purity, in excellent overall yield, avoiding organometallic reagents and wasteful by-production of R-enantiomers, from readily available S-citronellol, of the absolute stereochemical formula

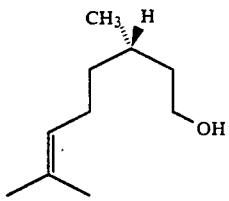

(IV)

The initial steps of this synthesis are conventional and involve optional protection of the alcohol group with a conventional silyl protecting group (such as t-butyldimethylsilyl group) followed by ozonolysis with methyl sulfide workup, to yield a novel compound of the absolute stereochemical formula

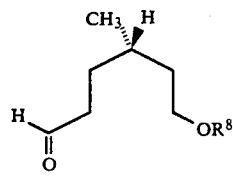

(V)

where $R^8$ is hydrogen (Va) or a silyl hydroxy protecting group (Vb). The methods used are specifically illustrated in Preparations below and are similar to those previously applied to R-citronellol in preparing the R-enantiomer of the compound of the above formula (V) wherein $R^8$ is t-butyldimethylsilyl. The latter, not useful here, was employed in the synthesis of proxiphomin (Tapolczay et al., J. Chem. Soc., Chem. Commun. 1985, pp. 143-145).

The present invention is specifically directed to intermediate compounds of the formula (V) and of the formula

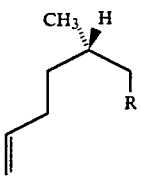

(VI)

(VIa) R=CH$_2$OR$^1$, R$^1$=a silyl protecting group
(VIb) R=CH$_2$OH
(VIc) R=CHO
(VId) R=COOH
(VIe) R=COCl and to a process for converting a compound of the formula (V) to the optically active acids of the formula (VId) and (II), which comprises the steps of:

(a) reacting a compound of the formula (V) with methylenetriphenylphosphorane

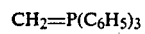

$CH_2=P(C_6H_5)_3$ to form a compound of the formula (VIa) or (VIb);

(b) dilute mineral acid hydrolysis when the compound is of the formula (VIa) to form the compound of the formula (VIb), carried out as a separate step or concurrently with the following step; and (c) oxidizing the compound of the formula (VIb) with chromic anhydride in dilute mineral acid to form the S-3-methyl-6-heptenoic acid of the formula (VId); and if desired, (d) catalytic hydrogenation of the compound of the formula (VId) to form S-3-methylheptanoic acid of the formula (II).

$R^8$ as hydrogen has the advantage of fewer steps, but $R^8$ as a silyl protecting group has the advantage of more facile purification when isolating the intermediate product from step (a). The preferred hydroxy protecting groups are trimethylsilyl, p-t-butylphenethyldimethylsilyl and t-butyldimethylsilyl. The preferred dilute mineral acid is H$_2$SO$_4$. It is preferred to synthesize the compound of the formula (Va) by ozonolysis of S-citronellol with methylsulfide work-up; and the compound of the formula (Vb), when $R^8$ is t-butyldimethylsilyl, by the further steps of:

(e) reacting S-citronellol with t-butyldimethyl silyl chloride; and (f) ozonolysis of the resulting hydroxy protected citronellol, with methyl sulfide work-up.

The present invention is also directed to an improved process for the preparation of the immunoregulatory agent of the formula (I) which comprises the steps of (a) coupling an activated form of S-3-methyl-6-heptenoic acid (e.g., the acid chloride, VIe) with a compound of the formula

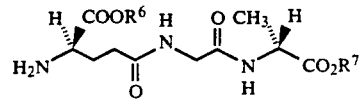

(VII)

wherein $R^6$ and $R^7$ are each benzyl, or one of $R^6$ and $R^7$ is benzyl and the other is (C$_1$-C$_6$)alkyl or (C$_6$-C$_8$)cycloalkylmethyl, in a reaction inert solvent to form an intermediate compound of the above formula (IIIb) where $R^3$ and $R^4$ correspond to $R^6$ and $R^7$; and (b) hydrogenation of said intermediate compound in a reaction inert solvent in the presence of a hydrogenation catalyst.

Finally, the present invention is directed to immunoregulatory agents and/or compound (I) precursors of the formula (III) above. The compound (IIIa) is obtained by conventional ester hydrolysis of a compound (IIIb).

The expression "reaction inert solvent" as employed herein refers to a solvent which does not interact with starting materials, intermediates or products in a manner which adversely affects the yield of the desired product. For example, by this definition water in the solvent of step (b), even though it may be directly or indirectly and favorably involved in the desired hydrolysis of the silyl ether, would be considered reaction inert by this definition.

DETAILED DESCRIPTION OF THE INVENTION

The present invention is readily carried out. S-Citronellol, which is available commercially, is first converted to one of the optically active starting materials of the formula (V) by conventional methods, as noted above and illustrated in Preparations below. The compound (V) is converted to S-3-methyl-6-heptenoic acid or S-3-methylheptanoic acid, of the above formulas (VId) and (II) respectively, in stepwise fashion as detailed in the following paragraphs.

In the first step, the hydroxy or hydroxy protected aldehyde (Va or Vb) undergoes the Wittig reaction with methylene triphenylphosphorane, generally freshly formed in situ from (methyl)triphenylphosphonium halide (conveniently the bromide) and butyllithium, in a reaction inert aprotic solvent, e.g., a mixture of tetrahydrofuran and hexane, e.g.,

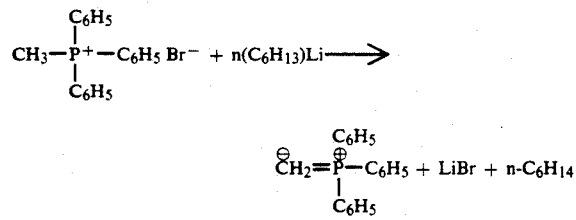

While temperature is not a critical feature of phosphorane formation, preferred temperatures are in the range $\pm 25°$ C., most preferably in the range $\pm 10°$ C. The aldehyde (Va) or hydroxy protected aldehyde (Vb) is then reacted with the phosphorane in like solvent and in a like temperature range, to form the hydroxy or hydroxy protected olefin of the formula (VIb) or (VIa), respectively.

In the second step, required only when a hydroxy protecting group is present, said protecting group is removed by hydrolysis, most conveniently by means of the aqueous acid conditions employed in the third step, which is a Jones oxidation of the primary alcohol (VIb) to the acid (VId). The Jones oxidation employs so-called Jones reagent, an aqueous solution of $H_2CrO_4$ formed from $CrO_3$ and a strong acid. Typically, Jones reagent is prepared from an excess of concentrated $H_2SO_4$ and $CrO_3$ with about 1:1 by weight of water, then diluted to the desired concentration, e.g., about 3M, with water. The alcohol (Va) protected alcohol (Vb), generally in solution in a water miscible, reaction inert organic solvent such as acetone is reacted with at least two molar equivalents of Jones reagent. Under these conditions, there is rapid hydrolysis of any silyl ether group to form the alcohol (VIb), which is then oxidized to the acid (VId). Temperature is not critical, e.g., $0°-50°$ C. is usually satisfactory, with ambient temperature, e.g., $17°-27°$ C. most convenient.

The Jones oxidation occurs via initial oxidation of the alcohol to the aldehyde of the formula (VIc), not usually isolated in the Jones oxidation. If isolation of the intermediate aldehyde is desired, the alcohol is oxidized with a more selective oxidizing agent, such as pyridinium chlorochromate, which will cleanly yield the intermediate aldehyde (VIc), which in turn is oxidized (with Jones reagent or another suitable reagent) to the acid (VId).

If desired, the unsaturated acid (VId), in activated form [e.g., as the acid chloride of the formula (VIe), as a conventional mixed anhydride, or activated by a conventional dehydrative coupling agent such as dicyclohexylcarbodiimide] is coupled in a conventional manner with the compound of the formula

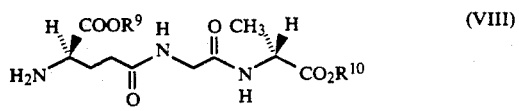

wherein $R^9$ and $R^{10}$ are each independently $(C_1-C_6)$alkyl, $(C_6-C_8)$cycloalkylmethyl or benzyl, to form the diester of the formula (IIIb). If desired, the latter is hydrolyzed by conventional methods to the immunoregulatory compound of the formula (IIIa) or a pharmaceutically acceptable salt thereof. Alternatively, the compound of the formula (IIIb), when $R^3$ and $R^4$ correspond to $R^6$ and $R^7$ as defined above, is hydrogenated to form the immunoregulatory compound of formula (I). In this hydrogenation, both the double bond is saturated with hydrogen and benzyl group(s) are hydrogenolized. The hydrogenation is carried out in a reaction inert solvent over a hydrogenation catalyst, e.g., nickel or a noble metal; supported (e.g., Raney nickel, Pd/C) or unsupported (e.g. $RhCl_3$). Solvent, temperature and pressure are not critical. Suitable solvents include, but are not restricted to lower alcohols, ethers such as dioxane, tetrahydrofuran or dimethoxyethane, and esters such as ethyl acetate. Preferably ambient temperature is employed without cooling, even if the reaction is somewhat exothermic, avoiding the cost of heating or cooling. Pressure is not critical, but will preferably be below 7 atmospheres in order to avoid expensive, high pressure equipment. Hydrogenation over Pd/C at pressures which are 3-6 times atmospheric pressure is particularly well suited for the present transformations.

Alternatively, the unsaturated acid of the formula (VId) is hydrogenated under conditions identical to those detailed in the preceding paragraph to yield S-3-methylheptanoic acid. Finally the S-3-methylheptanoic acid is activated in the manner detailed above and coupled with diester of the formula (VII) above, then hydrogenated as detailed above to form the immunoregulatory compound of the formula (I) above.

The present crystalline form the compound of the formula (I), wherein $R^3$ and $R^4$ are both hydrogen, is obtained by crystallization from an organic solvent or a combination of organic solvents. Suitable solvents are acetone, acetonitrile/ethanol or tetrahydrofuran/ether. The preferred solvent in terms of product recovery is acetonitrile/ethanol, but in terms of product purity, acetone is preferred. This novel crystalline form has definite stability advantages over the prior amorphous lyophilate. It is much more readily handled, being more dense and very much less electrostatic, permitting the preparation of more sophisticated dosage forms.

The pharmaceutically acceptable mono- or dibasic salts of the compound of the formula (I) or (IIIa) are generally obtained by treating a solution, preferably an aqueous solution of the free acid with a base such as NaOH, KOH, NaCO$_3$ or an amine, generally in the appropriate stoichiometric proportions. The salts are isolated by evaporation or by precipitation.

The products of this invention of the formula (I) or (III) are useful as agents in mammals, including humans, for the clinical and therapeutic treatment of diseases caused by various pathogenic microorganisms, especially gram-negative bacteria. They are also useful as immunostimulants in mammals, including humans, having an increased risk of infection due to existing or clinically-induced immunosuppression.

The test procedure employs normal or immunocompromised C$_3$H/HeN male mice from the Charles River Breeding Laboratory. The mice are acclimatized for 5 days before use and then treated either subcutaneously (SC) or orally (PO) with various dilutions (100, 10, 1 and 0.1 mg/kg) of the test compound or placebo (pyrogen free saline) using a volume of 0.2 ml. The treatment regiment was dependent on the infectious organism utilized: 24 and 0 hours before challenge for *Klebsiella pneumoniae* in normal mice; and 3, 2 and 1 day(s) before challenge for *Escherichia coli* or *Staph. aureus* in immunocompromised mice. The challenge is administered intramuscularly (IM) in the hip in the case of *K. pneumoniae* or intraperitoneally (IP) in the case of *E. coli* and *Staph. aureus*. A volume of 0.2 ml. was used for the challenge. Mortality was recorded after 7 days in the case of *K. pneumoniae* and after 3 days in the case of the other two microorganism challenges. Culture Preparation:

*K. pneumoniae, E. coli,* or *Staph. aureus:* the culture was streaked for purity from frozen blood stock on brain heart infusion (BHI) agar. Three colonies were picked from the 18 hour plate culture and placed into 9 ml. of BHI broth. The broth culture was grown for 2 hours at 37° C. on a rotary shaker after which 0.2 ml. was streaked on the surface of several BHI agar slants. Following an 18 hour incubation at 37° C., the slants were washed with BHI broth, the culture density adjusted using a spectronic 20 and the appropriate dilution made to achieve an LD90 challenge level in normal mice.

When used as antiinfective or immunostimulant agents in humans, the compounds (I) or (III) of this invention are conveniently administered via the oral, subcutaneous, intramuscular, intravenous or intraperitoneal routes, generally in composition forms, which are standard in pharmaceutical practice. For example, they can be admnistered in the form of tablets, pills, powders or granules containing such excipients as starch, milk sugar, certain types of clay, etc. They can be administered in capsules, in admixtures with the same or equivalent excipients. They can also be administered in the form of oral suspensions, solutions, emulsions, syrups and elixirs which may contain flavoring and coloring agents. For oral administration of the therapeutic agents of this invention, tablets or capsules containing from about 50 to about 500 mg. of the active component are suitable for most applications.

The physician will determine the dosage which will be most suitable for an individual patient and it will vary with the age, weight and response of the particular patient and the route of administration. The favored oral dosage range is from about 1.0 to about 300 mg/kg/day, in single or divided doses. The favored parenteral dose is from about 1.0 to about 100 mg/kg/day; the more favored range being from about 1.0 to about 20 mg/kg/day.

The following examples are given by way of illustration and are not to be construed as limitations of this invention, many variations of which are possible within the scope and spirit thereof.

EXAMPLE 1

S-7-(t-Butyldimethylsilyloxy)-5-methyl-1-heptene

In a 500 ml. 4-necked round bottom flask equipped with a stirrer, thermometer, N$_2$ inlet and addition funnel, (methyl)triphenylphosphonium bromide (25.7 g., 0.072 mol, 1.25 equiv.) was slurried in 77 ml. THF (tetrahydrofuran) and cooled in an acetone/wet ice bath. n-Butyllithium (43.2 ml. of 1.6N in hexane, 0.069 mol, 1.20 equiv.) was placed in the addition funnel. With the slurry initially at $-8°$ C., the butyllithium was added over 1 hour as the temperature rose and was held at $\pm 1°$ C. The mixture was stirred an additional 0.5 hour at 0°-2° C. to assure complete formation of intermediate methylenetriphenylphosphorane in a thin suspension of LiBr. The aldehyde product of Preparation 2 (14.1 g., 0.0576 mol) in 14 ml. THF was added portionwise over 40 minutes, maintaining the temperature at 3°-7° C. After stirring an additional 15 minutes, no starting aldehyde was detected by tlc using 3:1 hexane:ether as eluant (Rf starting aldehyde 0.6; Rf product 0.95). The reaction mixture was warmed to ambient temperature and diluted with 150 ml. ethylacetate and 90 ml. H$_2$O. The organic layer was separated and washed 2×100 ml. H$_2$O. The three aqueous layers were combined and backwashed with 40 ml. ethyl acetate. The organic layers were combined, dried over MgSO$_4$ and stripped to an oil, 25 g., which was triturated with 10 ml. hexane, filtered on a sinter glass funnel, the solids repulped in place with the 4× 10 ml. hexane, and the combined hexane filtrate and wash stripped to yield title product as an oil, 13.5 g. (96.6%); $^1$H-nmr (CDCl$_3$) delta (ppm) includes 5.4–6.2 (m, =CH), 4.8–5.3 (m, =CH$_2$), 3.7 (t, J=6.5 Hz, —OCH$_2$—), 0.08 (s, C(CH$_3$)$_3$) and 0.0 (s, Si(CH$_3$)$_2$), contaminated with 8 mol % (C$_6$H$_5$)$_3$PO (7.6, s, 1.25 H).

EXAMPLE 2

S-3-Methylhept-6-en-1-ol

Method A

By the method of the preceding Example, except to use 2.2 equivalents of each of methyl(triphenylphosphonium bromide and n-butyllithium, the aldehyde product of Preparation 6 (26.3 g., 0.20 mol; corrected for purity) was reacted with methylenetriphenylphosphorane. Although the formation of gummy solid was noted during the addition of the aldehyde solution, the reaction became a thin slurry once warmed to ambient temperature for work-up. The reaction mixture was diluted with 500 ml. H$_2$O and 300 ml. ethyl acetate. The layers were separated and washed 3×250 ml. H$_2$O. The combined aqueous layers were back-washed 2×300 ml. ethyl acetate. The three organic layers were combined, dried over MgSO$_4$ and stripped to yield 65.7 g. of oil containing 25.6 g. (100%) of title product and about 40 g. of triphenylphosphine oxide, suitable for further processing in Example 4 below.

Method B

Pure title product is more readily obtained by conventional hydrolysis of the product of Example 1, e.g., in the dilute sulfuric acid of Example 4 below. Title product is isolated by extraction into ethyl acetate, drying over MgSO$_4$ and stripping.

EXAMPLE 3

S-3-Methyl-6-heptenal

The title product of the preceding Example (1.14 g., 0.01 mol) is dissolved in 20 ml. CH$_2$Cl$_2$ and cooled to 0° C. Pyridinium chlorochromate (4.30 g., 0.02 mol) is added portionwise, maintaining the temperature at 0°-5° C. The mixture is warmed to ambient temperature, stirred 2 hours, filtered through a pad of silica gel, and the filtrate stripped to yield title product as an oil, which if desired is further purified by distillation.

EXAMPLE 4

S-3-Methyl-6-heptenoic Acid

Method A

In a 2000 ml. 3-necked round bottom flask equipped with stirrer, thermometer and addition funnel title product of Example 1 (81 g., corrected for purity, 0.33 mol) was dissolved in 400 ml. acetone and cooled to 0°-5° C. In a separate flask, CrO$_3$ (72.1 g., 0.72 mol was mixed with 50 ml. H$_2$O and stirred at 0°-5° C. and 62.1 ml. concentrated H$_2$SO$_4$ slowly added, and the mixture diluted to 250 ml. with H$_2$O to yield a 2.88 M solution of H$_2$CrO$_4$ (Jones reagent). The latter solution (240 ml., 0.67 mol) was added portionwise to the above acetone solution over 1.2 hours. The temperature rapidly rose to 17° C., and was maintained at 17°-25° C. as the reagent was added. By the end of the addition there was no exotherm. The mixture was recooled to 6° C., 70 ml. of 2-propanol added over 10 minutes (during which the temperature rose to 20° C.), and then concentrated in vacuo to an oil to which was added with stirring 400 ml. 5N NaOH over 50 minutes, maintaining temperature 22°±5° C. The thick reaction mixture was diluted with 400 ml. of H$_2$O and filtered over diatomaceous earth. The wet cake was repulped in 400 ml. H$_2$O and 50 ml. 5N NaOH, warmed on a steam bath and refiltered. The combined filtrates were washed 3×300 ml. isopropyl ether. The combined organic layers were back extracted with 200 ml. 2N NaOH. The combined aqueous layers were acidified to pH 1.0 by the slow addition of 50 ml. concentrated HCl and product extracted into 3×300 ml. fresh isopropyl ether. The organic extracts were combined and stripped to yield title product as an oil, 29.1 g. (61%). An additional 7.7 g. (16%) was obtained by a second basic extraction of the diatomaceous earth filter cake followed by like isolation. $^1$H-nmr of the combined product (CDCl$_3$) delta (ppm) includes 11.9 (s, —COOH), 5.8 (m, =CH), 5.0 (m, =CH$_2$) and 1.0 (d, —CH$_3$) and isopropyl ether peaks at 3.7 and 1.1 showing contamination with 8.6 mol % (6.3 weight %) of isopropyl ether, which does not interfere with the use of this product in further processing.

Method B

The product of Method A of Example 2 (65.7 g., containing 26.3 g., 0.20 mol of S-3-methylhept-6-en-1-ol) was oxidized according to Method A of the present Example. After isopropanol quench and stirring for 1 hour at 0°-5° C., by which time the reaction mixture was completely green, organic solvents were stripped, and the aqueous residue diluted with 250 ml. H$_2$O and extracted 3×250 ml. isopropyl ether. The organic extracts were combined and treated with 160 ml. 2N NaOH, leading to heavy precipitation of (C$_6$H$_5$)$_3$PO (contaminant in the starting material) which was recovered by filtration with thorough 1N NaOH wash. The filtrate and wash were combined, the layers were separated and the organic layer washed with 80 ml. additional 1N NaOH. All aqueous layers were combined, washed 3×250 ml. isopropyl ether, acidified with 50 ml. concentrated HCl to pH 1.0, and the desired product extracted into 3×250 ml. fresh isopropyl ether. The combined acidic organic extracts were dried over MgSO$_4$ and stripped to yield title product, 14.0 g., which, if desired, is further purified by distillation.

EXAMPLE 5

S-3-Methylheptanoic Acid

A Paar hydrogenation bottle was charged with 10% Pd/C (1.64 g. of 50% water wet), 150 ml. ethyl acetate and the unsaturated acid of the preceding Example (3.28 g., corrected for purity) and the slurry hydrogenated at 4×atmospheric pressure for 1.5 hours by which time H$_2$ uptake was complete. Catalyst was recovered by filtration over diatomaceous earth and the filtrate stripped to yield title product as an oil, 3.20 (96%).

Alternatively, 5% Pd/C (2 g. of 50% water wet) and then title product of the preceding Example (33.3 g. corrected for purity) in 150 ml. ethyl acetate was charged to a 1 liter autoclave and hydrogenated at 4×atmospheric pressure for 2 hours at 30°-31° C., by which time H$_2$ uptake was complete. Catalyst was recovered by filtration over diatomaceous earth and the filtrate stripped to an oil, 35.4 g., which was distilled under high vacuum to yield purified title product, 29.6 g. (87.6%); b.p. 77°-79° C./0.2 mm; $^1$H-nmr (CDCl$_3$) delta (ppm): 12.0 (s, —COOH), 1.0 (d, —CH$_3$), 0.6-2.8 (m, remaining 13H); ir (film) 3400-2400, 2960, 2925, 2860, 1708, 1458, 1410, 1380, 1295, 1228, 1190, 1152, 1100, 930 cm$^{-1}$; [alpha]$_D^{25}$ = −6.41° (C=1% in CH$_3$OH); $n_D^{22.5}$ = 1.427.

EXAMPLE 6

S-3-Methylheptanoyl Chloride

The acid product of the preceding Example (8.5 g., 0.062 mol) was dissolved 18 ml. CH$_2$Cl$_2$. Oxalyl chloride (5.36 ml., 7.80 g., 0.0614 mol) was mixed into the solution and the mixture allowed to stand for 4 hours, by which time the reaction was complete, as evidenced by the lack of further gas evolution. This solution of acid chloride was immediately used directly in Example 8, Method C. Alternatively, the acid chloride was isolated by stripping away the solvent, for use in Method A of Example 8, and, if desired, was further purified by distillation, bp 45°/1.5 mm.

EXAMPLE 7

S-3-Methyl-6-heptenoyl Chloride

The acid product of Example 4 (0.747 g., 5 mmol) was converted to a $CH_2Cl_2$ solution of title product by the method of the preceding Example and used directly in Example 9 below. Alternatively the reaction mixture is stripped to yield title product, which, if desired, is distilled at reduced pressure.

EXAMPLE 8

N-(S-3-Methylheptanoyl)-D-gamma-glutamyl(alpha benzyl ester)-glycyl-D-alanine Benzyl Ester

Method A

To a solution of 1.0 g. (2.03 mmol) of D-gamma-glutamyl (alpha benzyl ester)-glycyl-D-alanine benzyl ester hydrochloride (Preparation 5) and 616 mg. (6.09 mmol) of triethylamine in 50 ml. of methylene chloride was added 660 mg. (4.06 mmol) of S-3-methylheptanoyl chloride and the reaction mixture stirred at room temperature for 80 hours. The methylene chloride was evaporated in vacuo and the residue dissolved in ethyl acetate. The resulting solution was washed sequentially with 2.5% hydrochloric acid, water, 10% potassium carbonate, water, and a brine solution. The organic phase was separated, dried over magnesium sulfate and concentrated under vacuum. The residue was triturated with diethyl ether and filtered under nitrogen to yield title product, all of which was used directly in Example 10, Method A.

Method B

The product of Preparation 5 (0.75 g., 1.53 mmol), 5 ml. $CH_2Cl_2$ and triethylamine (0.212 ml., 1.53 mmol) were combined and stirred under $N_2$. S-3-methylheptanoic acid (Example 5; 0.20 g., 1.39 mmol) in 4 ml. $CH_2Cl_2$ and then dicyclohexylcarbodiimide (0.286 g., 1.37 mmol) were added and the mixture stirred for 16 hours. The reaction mixture was filtered, the filtrate stripped, the residue taken up in 10 ml. ethyl acetate, and the solution washed in sequence with 5 ml. 2.5% HCl, 5 ml. $H_2O$, 5 ml. 10% $K_2CO_3$ and 5 ml. of brine, dried over $MgSO_4$ to yield 71 mg. (88%) of title product.

Method C

In a 500 ml. 4-necked round bottom flask equipped with stirrer, thermometer dropping funnel and $N_2$ inlet, the product of Preparation 5 (32.8 g., 0.059 mol) was dissolved in 175 ml. $CH_2Cl_2$ and cooled to 0°–5° C. Maintaining that temperature range, triethylamine (24.7 ml., 17.9 g., 0.177 mol, 3 equiv) was added as a slow stream over 15 minutes. The ice-water bath was maintained and the entire batch of S-3-methylheptanoyl chloride in $CH_2Cl_2$ from Example 6 added over 15 minutes as the temperature rose to 21° C. Stirring in the ice-water bath was continued for 45 minutes, by which time the gelatinous mixture became too thick to stir. The gelatinous mass was broken up and mixed with 125 ml. of 10% HCl and 50 ml. $CH_2Cl_2$. The organic layer was separated, washed sequentially 2×125 ml. $H_2O$, 2×125 ml. 10% $K_2CO_3$ and 1×125 ml. $H_2O$, dried over $MgSO_4$ and stripped to 82.3 g. of damp, white solids. These solids were taken up in 500 ml. of hot ethyl acetate. On slow cooling to ambient temperature, title product crystallized heavily, and the mixture was diluted with an additional 40 ml. ethyl acetate in order to maintain facile stirring. Purified title product was recovered by filtration and vacuum dried at 40° C., 31.1 g., (90.5%).

$^1$H-nmr ($CDCl_3$) delta (ppm): 8.4–8.1 (m, 3H), 7.15 (s, 10H), 5.1 (s, 4H), 4.4–4.2 (m, 2H), 3.7 (d, 2H), 2.2 (t, 2H), 2.1–1.7 (m, 6H), 1.4–1.1 (m, 10H), 0.92–0.8 (m, 6H).

EXAMPLE 9

N-(S-3-Methyl-6-heptenoyl)-D-gamma-glutamyl(alpha benzyl ester)-glycyl-D-alanine Benzyl Ester By Method C of the preceding Example, the product of Preparation 5 (2.77 g., 5 mmol) was coupled with the entire batch of acid chloride in $CH_2Cl_2$ from Example 7. The initially obtained product, 2.77 g., recovered by stripping the washed and dried organic layer, was taken up in 20 ml. hot ethyl acetate, the solution diluted with 20 ml. hexane, cooled and purified product recovered by filtration, 2.24 g. (77%), m.p. 137.5–139.5.

EXAMPLE 10

N-(S-3-Methylheptanoyl)-D-gamma-glutamylglycyl-D-alanine

Method A

The entire product of Method A of Example 8 was dissolved in 65 ml. of methanol. Palladium hydroxide (250 mg.) was added to the solution and the mixture shaken in a hydrogen atmosphere at 4 atmospheres pressure for 3 hours. The catalyst was filtered and the solvent removed in vacuo. The residue was dissolved in water and lyophilized to give desired product.

The NMR spectrum (DMSO-$d_6$) showed absorption at 8.27–8.03 (m, 3H), 4.32–4.1 (m, 2H), 3.72 (d, J=6 Hz, 2H), 2.22 (t, J=8 Hz, 2H), 2.27–1.68 (m, 6H), 1.42–1.0 (m, 10H) and 0.94–0.8 (m, 6H).

When carried out on a weighed quantity of the title product of Example 8 (0.50 g.), using 90 mg. of 20% Pd(OH)$_2$/C (31% water wet), in 25 ml. $CH_3OH$, this method gave 0.24 g. of the same, fluffy, electrostatic title product; ir (nujol mull) 3300, 2940, 1740, 1650, 1540, 1468 and 1380 cm$^{-1}$; all but the last two peaks are broad and poorly resolved.

Method B

The product of Method C of Example 8 (30.8 g.) was slurried in 300 ml. absolute ethanol in a 2 liter autoclave. 5% Pd/C, 1.54 g., 50% water wet) was added and the mixture hydrogenated at 4×atmospheric pressure for 1 hour, by which time uptake of hydrogen was complete. The catalyst was recovered by filtration, first over paper, then over 0.45 micron nylon milipore, employing 100–150 ml. ethanol for transfer and wash. The combined filtrate and wash liquors were stripped to a damp, white solid, which was dissolved in 150 ml. of a hot, 1:10 mixture of absolute ethanol and acetonitrile, clarified by hot filtration, boiled down to 35 ml., slowly cooled to room temperature, granulated and filtered to yield crystalline, dense, non-electrostatic title product, 20.1 g. (94%) characterized by its ir (nujol mull) which includes major, well-resolved, sharp peaks at 3340, 3300, 2900, 2836, 1725, 1650, 1628, 1580, 1532, 1455, 1410, 1370, 1280, 1240, 1216 and 1175 cm$^{-1}$.

Method C

Crystalline product (9.4 g.), prepared according to immediately preceding Method B, was dissolved in 1000 ml. of acetone by heating at reflux for 1 hour. The solution was cooled to room temperature and seeded with a trace of Method B product to induce crystallization. After stirring for 6 hours, further purified title product was recovered by filtration with minimal acetone wash and dried in vacuo at 35° C., 7.25 g., having identical ir peaks to those of the acetonitrile/ethanol crystals of Method B.

Method D

The product of the preceding Example (0.50 g.) was combined with 0.026 g. of 5% Pd/C (50% water wet) in 125 ml. of absolute ethanol in a Paar hydrogenation bottle. The mixture was hydrogenated under 4×atmospheric pressure of hydrogen for 2.5 hours. Catalyst was recovered by filtration and the filtrate stripped to yield title product as tackey solids which are crystallized according to the immediately preceding Method.

EXAMPLE 11

N-(S-3-Methyl-6-heptenoyl)-D-gamma-glutamylglycyl-D-alanine

The product of Example 9 (1 g.) is dissolved in 5 ml. $CH_3OH$. 1N NaOH (2.50 ml.) is added and the mixture stirred 3 hours at ambient temperature. The $CH_3OH$ is stripped and the aqueous residue diluted with 7.5 ml. $H_2O$, extracted 2×7.5 ml. ethyl acetate, and acidified to pH 3.0 with 1N HCl. The acidified aqueous is extracted continuously with fresh ethyl acetate, and the extract stripped to yield title product which is converted to a lyophilate according to Method A of Example 10.

EXAMPLE 12

N-(S-3-Methyl-6-heptenoyl)-D-gamma-glutamyl (alpha benzyl ester)-glycyl-D-alanine Butyl Ester D-gamma-glutamyl(alpha benzyl ester)-glycyl-D-alanine butyl ester (Preparation 5) is coupled with S-3-methyl-6-heptenoyl chloride (Example 7) by Method A of Example 8 to yield present title product.

EXAMPLE 13

N-(S-3-Methylheptanoyl)-D-gamma-glutamylglycyl-D-alanine Butyl Ester

By the hydrogenation methods of Example 10, the product of the preceding method is converted to present title product.

PREPARATION 1

O-(t-Butyldimethylsilyl)-S-citronellol

In a 500 ml. 4-necked round bottom flask equipped with stirrer, thermometer, $N_2$ inlet and addition funnal, S-citronellol (547 g., 3.5 mol) was dissolved in 547 ml. DMF (dimethylformamide) at ambient temperature (21° C.). Imidazole (262.1 g., 3.85 mol, 1.1 equiv) was added. The temperature fell to 13° C. and was further reduced to −6.5° with an ice/acetone bath. t-Butyldimethylchlorosilane (580.3 g., 3.85 mol, 1.1 equiv), previously dissolved by vigorous stirring in 1160 ml. DMF, was added over 1.25 hours, allowing the temperature to slowly rise to 11° C. over the same time period. After an additional 0.25 hour, tlc (3:1 hexane:ether) indicated complete conversion to desired product (Rf starting material 0.2; Rf product, 0.9).

To isolate, the mixture was added to 500 ml. hexane and 1000 ml. ice and water. The layers were separated and the organic layer washed with 2000 ml. ice cold 0.25N HCl. The two aqueous layers were combined and back washed with 500 ml. hexane, which was combined with the original organic layer, washed with 500 ml. saturated $NaHCO_3$, dried over $MgSO_4$ and stripped to produce a quantitative yield of title product, 986.7 g., 104% of theory due to minor retention of solvent; $^1$H-nmr ($CDCl_3$) delta (ppm) includes 5.2 (t, J=7 Hz, =CH), 3.65 (t, J=6.5 Hz, —O—$CH_2$—)), 1.7 and 1.65 (2S, 2=C($CH_3$)), 0.8 (s, —SiC($CH_3$)$_3$), and 0.0 (s, —Si($CH_3$)$_2$).

PREPARATION 2

S-6-(t-Butyldimethylsilyloxy)-4-methylhexanal

In a 500 ml. 4-necked round bottom flash, equipped with a mechanical stirrer, a straight glass inlet for an $O_3/O_2$ stream, a thermometer and an outlet connected to a saturated KI trap, the product of the preceding preparation (81.2 g., corrected for solvent content, 0.30 mol) was dissolved in a 120 ml. $CH_2Cl_2$ and 81 ml. $CH_3OH$. $NaHCO_3$ (6.3 g., 0.075 mol, 0.25 equiv) was added and the mixture cooled to −10° C. in an acetone/dry ice bath. The temperature was further reduced and held at −72° to −75° C. as $O_3/O_2$ was bubbled into the reaction for 6 hours. After a little less than 1 hour, all of the $O_3$ was not absorbed by the reaction mixture, as evidenced by a yellow color forming in the KI trap. Tlc with hexane eluant indicated reaction was complete (Rf of starting material, 0.3; Rf of intermediate material, 0.0).

The reaction mixture was purged of excess $O_3$ with $N_2$, dimethyl sulfide (26.4 ml., 22.4 g., 0.36 mol, 1.2 equiv) added, the bath removed and the mixture allowed to warm to ambient temperature and stirred under $N_2$ for 16 hours, by which time tlc (6:1 hexane:ether) indicated no intermediate material remained (Rf of intermediate material, 0.8; Rf of product, 0.05). The mixture was then stripped and the residue which was distributed between 150 ml. ethyl acetate and 300 ml. $H_2O$. The organic layer was washed with 300 ml. fresh $H_2O$. The combined $H_2O$ layers were back washed with 150 ml. fresh ethyl acetate. The organic layers were combined, dried over $MgSO_4$ and stripped to an oil, ultimately for 16 hours under high vacuum to produce a quantitative yield of title product 74.7 g., 101.9% of theory due to minor solvent contamination; $^1$H-nmr ($CDCl_3$) delta (ppm) includes 9.75 (t, —CHO), 3.6 (t, J=6 Hz, —O—$CH_2$—), 0.9 (s, —SiC($CH_3$)$_3$), 0.0 (s, —Si($CH_3$)$_2$).

PREPARATION 3

Glycyl-D-alanine benzyl ester hydrochloride

To a cold (0° C.) solution of 100 ml. methylene chloride containing 10 g. (57 mmol) of N-t-butyloxycarbonylglycine, 20 g. (57 mmol) of D-alanine benzyl ester p-toluene sulfonic acid salt and 5.77 g. (57 mmol) of triethylamine was added 12.3 g. (60 mmol) of dicyclohexylcarbodiimide and the resulting action mixture allowed to warm to room temperature. After 18 hours the mixture was filtered and the filtrate concentrated in vacuo. The residue was dissolved in 200 ml. of ethyl acetate and the organic layer washed with 2.5% hydrochloric acid, water, a saturated sodium bicarbonate solution and a brine solution. The organic layer was separated, dried over magnesium sulfate and evaporated under reduced pressure. To the resulting oil 200 ml. of dioxane saturated with hydrogen chloride was added. After 30 minutes 40 ml. of diethyl ether was added and the product filtered under nitrogen, 10.9 g. (70% yield).

PREPARATION 4

N-t-Butoxycarbonyl-D-gamma-glutamyl (alpha benzyl ester)hydrosuccinamide ester

To 1500 ml. of methylene chloride containing 50 g. (143 mmol) of N-t-butoxycarbonyl-D-gamma-glutamic acid alpha-benzyl ester and 17.3 g. (150 mmol) of N-hydroxy-succinamide was added 30.9 g. (15 mmol) of dicyclohexylcarbodiimide and the resulting reaction mixture allowed to stir at room temperature for 18 hours. The solids were filtered and the filtrate concentrated in vacuo. The residue was triturated with diethyl ether and the solids filtered under nitrogen, 43.7 g. (68% yield).

PREPARATION 5

D-gamma-Glutamyl(alpha benzyl ester)-glycyl-D-alanine benzyl ester hydrochloride A solution containing 4.3 g. (9.45 mmol) of N-t-butoxycarbonyl-D-gamma-glutamyl (alpha benzyl ester) hydroxysuccinamide ester, 2.71 g. (9.92 mmol) of glycyl-D-alanine benzyl ester hydrochloride and 1.0 g. (9.92 mmol) of triethylamine in 100 ml. of methylene chloride was allowed to stir at room temperature for 18 hours, and was then concentrated in vacuo. The residue was dissolved in 200 ml. of ethyl acetate and the solution washed with 2.5% hydrochloric acid, water, 10% potassium carbonate and a brine solution. The organic phase was separated, dried over magnesium sulfate and evaporated under reduced pressure. The residue was treated with 200 ml. of dioxane saturated with hydrogen chloride and allowed to stir for 2 hours. The solution was concentrated to dryness in vacuo and the residue triturated with diethyl ether. The solids were filtered under nitrogen, 3.41 g. (73% yield).

By the same method the product of the preceding Preparation was coupled with glycyl-D-alanine butyl ester to form D-gamma-glutamyl(alpha benzyl ester)-glycyl-D-alanine butyl ester hydrochloride.

PREPARATION 6

S-6-Hydroxy-4-methylhexanal

Method A

In a 250 ml. 3-necked round bottom flask was equipped with magnetic stirrer, thermometer, gas inlet tube and gas outlet tube leading to gas-washing bottle containing saturated KI. The flask was charged with S-citronellol (31.25 g., 0.20 mol) in 81 ml. $CH_2Cl_2$ and 54 ml. $CH_3OH$ and cooled to $-8°$ C. Maintaining the temperature between $-2°$ and $-10°$ C., $O_2/O_3$ was bubbled through the reaction for 4.5 hours, by which time trapping of excess $O_3$ by the KI solution was indicated and complete reaction was indicated by a positive starch/KI paper test on the reaction mixture. The mixture was maintained at $-5°$ C., purged with $N_2$, and methyl sulfide (17.7 ml., 15.0 g., 0.24 mol) added. The reaction mixture was allowed to warm to ambient temperature, then stirred for 16 hours, by which time tlc using isopropyl ether as eluant indicated reaction to be complete (Rf of the S-citronellol, 0.7; Rf of the product, 0.4), and finally stripped of solvent to yield 50.8 g. of oil. The oil was diluted with 30 ml. of ethyl acetate and 25 ml. $H_2O$ resulting in a single phase. The further addition of 150 ml. of ether gave 2 phases. The layers were separated and the organic phase washed $2 \times 25$ ml. $H_2O$, dried over $MgSO_4$ and stripped to yield a colorless oil, 23.9 g. The combined aqueous layers were extracted $2 \times 50$ ml. ethyl acetate, and the extracts combined, dried and stripped to yield an additional 7.8 g. of colorless oil. The colorless oils were combined and further stripped to produce title product, 28.3 g. (108.7% of theory) clean by tlc (as noted above) except for solvent contamination, appropriate for use in further reactions as described above.

Method B

The product of Preparation 2 is hydrolyzed by conventional methods, such as the dilute sulfuric acid of Example 4 above. Title product is isolated by extraction into ethyl acetate and stripping as in Method A immediately above.

We claim:

1. A process for the preparation of S-3-methylheptanoic acid which comprises the steps of:
   (a) reacting S-6-hydroxy-4-methylhexanal or S-6-(silyl protected)hydroxy-4-methylhexanal with methylene triphenylphosphorane in a reaction inert solvent to form S-7-hydroxy-5-methyl-1-heptene or S-7-(silyl protected)hydroxy-5-methyl-1-heptene;
   (b) when the product of step (a) contains a silyl protecting group, hydrolysis of said protecting group in dilute mineral acid to form said S-7-hydroxy-5-methyl-1-heptene, carried out as a separate step, or concurrently with the following step;
   (c) oxidation of said S-7-hydroxy-5-methyl-1-heptene with chromic anhydride in dilute mineral acid to form S-3-methyl-6-heptenoic acid; and
   (d) catalytic hydrogenation of the double bond in said 6-heptenoic acid to form said S-3-methylheptanoic acid.

2. A process of claim 1 wherein S-6-hydroxy-4-methylhexanal is the reactant in step (a).

3. A process of claim 2 wherein the mineral acid is sulfuric acid.

4. A process of claim 1 wherein the required S-6-hydroxy-4-methylhexanal is prepared by ozonolysis of S-citronellol.

5. A process of claim 1 wherein S-6-(silyl protected)-hydroxy-4-hexanal is the reactant in step (a), and steps (b) and (c) are carried out concurrently.

6. A process of claim 5 wherein the silyl protecting group is t-butyldimethylsilyl.

7. A process of claim 6 wherein the mineral acid is sulfuric acid.

8. A process of claim 6 wherein the required S-6-(t-butyldimethylsiloxy)-4-methylhexanal is prepared by the further steps of:
   (e) reacting S-citronellol with t-butyldimethylsilyl chloride; and
   (f) ozonolysis of the resulting hydroxy protected citronellol.

* * * * *